US00RE47452E

(19) United States
(12) Reissued Patent
Bui et al.

(10) Patent Number: US RE47,452 E
(45) Date of Reissued Patent: Jun. 25, 2019

(54) ANTIMICROBIAL HOUSING AND COVER FOR A MEDICAL DEVICE

(71) Applicants: Baxter International Inc., Deerfield, IL (US); Baxter Healthcare SA, Glattpark (Opfikon) (CH)

(72) Inventors: Tuan Bui, Chicago, IL (US); Ton That Hai, Round Lake, IL (US); Mark Nordhaus, Antioch, IL (US); Paul Sanders, Greendale, WI (US); Cong Jiang, Gurnee, IL (US); David Lamb, Cary, IL (US); Ozlem Yardimci, Lake Forest, IL (US); Kent L. Lurvey, Grayslake, IL (US); Vadim V. Krongauz, Bartlett, IL (US)

(73) Assignees: Baxter International Inc., Deerfield, IL (US); Baxter Healthcare SA, Glattpark (Opfikon) (CH)

(21) Appl. No.: 15/446,651

(22) Filed: Mar. 1, 2017

Related U.S. Patent Documents

Reissue of:
(64) Patent No.: 9,125,973
Issued: Sep. 8, 2015
Appl. No.: 12/759,437
Filed: Apr. 13, 2010

U.S. Applications:
(63) Continuation-in-part of application No. 11/780,917, filed on Jul. 20, 2007, now Pat. No. 7,981,381, and a continuation-in-part of application No. 11/780,876, filed on Jul. 20, 2007, now abandoned.

(51) Int. Cl.

| | |
|---|---|
| ***A61M 39/04*** | (2006.01) |
| ***A61L 31/14*** | (2006.01) |
| ***A61L 27/34*** | (2006.01) |
| ***A61L 27/50*** | (2006.01) |
| ***A61L 27/54*** | (2006.01) |
| ***A61L 29/08*** | (2006.01) |
| ***A61L 29/14*** | (2006.01) |
| ***A61L 29/16*** | (2006.01) |
| ***A61L 31/10*** | (2006.01) |
| ***A61L 31/16*** | (2006.01) |
| ***C07D 213/30*** | (2006.01) |
| ***C08J 9/36*** | (2006.01) |
| *A61M 39/16* | (2006.01) |

(52) U.S. Cl.
CPC ..... *C08J 9/36* (2013.01); *A61L 27/34* (2013.01); *A61L 27/50* (2013.01); *A61L 27/54* (2013.01); *A61L 29/085* (2013.01); *A61L 29/14* (2013.01); *A61L 29/16* (2013.01); *A61L 31/10* (2013.01); *A61L 31/14* (2013.01); *A61L 31/16* (2013.01); *C07D 213/30* (2013.01); *A61L 2300/404* (2013.01); *A61L 2300/442* (2013.01); *A61L 2400/18* (2013.01); *A61L 2420/02* (2013.01); *A61M 39/045* (2013.01); *A61M 39/16* (2013.01); *C08J 2207/10* (2013.01); *C08J 2309/06* (2013.01); *C08J 2345/00* (2013.01); *C08J 2367/00* (2013.01); *C08J 2369/00* (2013.01); *C08J 2375/04* (2013.01); *C08J 2377/00* (2013.01)

(58) Field of Classification Search
CPC ..... C08J 9/36
USPC ..... 424/423; 252/586
See application file for complete search history.

(56) References Cited

U.S. PATENT DOCUMENTS

| | | | |
|---|---|---|---|
| 4,045,400 | A | 8/1977 | Korshak et al. |
| 4,247,498 | A | 1/1981 | Castro |
| 4,432,766 | A | 2/1984 | Bellotti et al. |
| 4,502,605 | A | 3/1985 | Wloszczyna |
| 4,539,256 | A | 9/1985 | Shipman |
| 4,618,533 | A | 10/1986 | Steuck |
| 4,677,076 | A | 6/1987 | Langhals |
| 4,739,881 | A | 4/1988 | Bruso |
| 4,828,797 | A | 5/1989 | Zwarun et al. |
| 4,839,291 | A | 6/1989 | Welsh et al. |
| 4,847,088 | A | 7/1989 | Blank |

(Continued)

FOREIGN PATENT DOCUMENTS

| | | |
|---|---|---|
| EP | 0183396 | 6/1986 |
| EP | 0517050 | 12/1992 |

(Continued)

OTHER PUBLICATIONS

Kaler et al., "Probing Structure of Blood Plasma Proteins with Solvatochromic Fluorescent Probes, Nile Red and Its Derivatives," SPIE, vol. 2980, pp. 484-489.
Mohr, "Materials and Polymers in Optical Sensing," Institute of Physical Chemistry, pp. 1-23. 2002.
Crowther et al., "Covalent Immobilisation of Solvatochromic Dyes," J. Chem. Soc. Chem. Commun, 1995, p. 2445.
Rosett et al., "Antimicrobial Activity of Heparin," J. Clin. Microbiol. 1980, 11(1), 30-34.

(Continued)

*Primary Examiner* — Timothy J. Kugel
(74) *Attorney, Agent, or Firm* — K&L Gates LLP

(57) ABSTRACT

A method for immobilizing dyes and antimicrobial agents on a polymeric cover or housing for a medical device is disclosed and described. The surface may be that of a catheter, a connector, a drug vial spike, a bag spike, a prosthetic device, an endoscope, a surface of an infusion pump, a key pad, a touch screen or a handle. The surfaces may also be one or more of those associated with a infusion of a medicament or dialysis treatment, such as peritoneal dialysis or hemodialysis, where it is important that the working surface for the dialysis fluid be sterile. These surfaces include connectors for peritoneal dialysis sets or for hemodialysis sets, bag spikes, dialysis catheters, and so forth. A method for determining whether a surface has been sterilized, and a dye useful in so indicating, is also disclosed.

8 Claims, 2 Drawing Sheets

(56) References Cited

U.S. PATENT DOCUMENTS

| | | | | |
|---|---|---|---|---|
| 4,867,881 | A | 9/1989 | Kinzer | |
| 5,024,875 | A | 6/1991 | Hill et al. | |
| 5,057,303 | A | 10/1991 | Casey | |
| 5,096,813 | A | 3/1992 | Krumhar et al. | |
| 5,132,108 | A * | 7/1992 | Narayanan et al. | A61L 33/0029 424/422 |
| 5,135,489 | A | 8/1992 | Jepson et al. | |
| 5,185,450 | A | 2/1993 | Owen | |
| 5,242,432 | A | 9/1993 | DeFrank | |
| 5,360,413 | A | 11/1994 | Leason et al. | |
| 5,405,736 | A | 4/1995 | Young | |
| 5,443,987 | A | 8/1995 | DeCicco et al. | |
| 5,674,206 | A | 10/1997 | Allton et al. | |
| 5,690,612 | A | 11/1997 | Lopez et al. | |
| 5,730,418 | A | 3/1998 | Feith et al. | |
| 5,780,098 | A | 7/1998 | Battles | |
| 5,782,816 | A | 7/1998 | Werschmidt et al. | |
| 5,895,627 | A | 4/1999 | Khachatoorian | |
| 5,900,067 | A | 5/1999 | Jones | |
| 6,039,302 | A | 3/2000 | Cote, Sr. et al. | |
| 6,045,539 | A | 4/2000 | Menyhay | |
| 6,063,587 | A | 5/2000 | Ishiyama et al. | |
| 6,063,631 | A | 5/2000 | Ignacio | |
| 6,126,826 | A | 10/2000 | Pacheco et al. | |
| 6,150,430 | A | 11/2000 | Walters et al. | |
| 6,238,623 | B1 | 5/2001 | Amhof et al. | |
| 6,246,824 | B1 | 6/2001 | Vandeberg et al. | |
| 6,265,476 | B1 | 7/2001 | Krongauz et al. | |
| 6,287,518 | B1 | 9/2001 | Ignacio et al. | |
| 6,346,417 | B1 | 2/2002 | Ignacio et al. | |
| D456,524 | S | 4/2002 | Hehenberger | |
| 6,368,558 | B1 | 4/2002 | Suslick et al. | |
| 6,383,815 | B1 | 5/2002 | Potyrailo | |
| 6,395,551 | B1 | 5/2002 | Kipke et al. | |
| 6,440,744 | B1 | 8/2002 | Ignacio et al. | |
| 6,472,451 | B2 | 10/2002 | Ha et al. | |
| 6,501,002 | B1 | 12/2002 | Roe et al. | |
| 6,506,814 | B2 | 1/2003 | Krongauz et al. | |
| 6,524,846 | B1 | 2/2003 | Robinson, Jr. | |
| 6,528,277 | B1 | 3/2003 | Hendricks et al. | |
| 6,551,555 | B2 | 4/2003 | Antonoplos et al. | |
| 6,596,657 | B1 | 7/2003 | Shalaby | |
| 6,623,955 | B2 | 9/2003 | Matner et al. | |
| 6,663,877 | B1 | 12/2003 | Appleton et al. | |
| 6,669,681 | B2 | 12/2003 | Jepson et al. | |
| 6,682,509 | B2 | 1/2004 | Lopez | |
| 6,706,537 | B2 | 3/2004 | Ignacio et al. | |
| 6,716,891 | B1 | 4/2004 | Meisenburg et al. | |
| 6,749,807 | B1 | 6/2004 | Schindly et al. | |
| 6,767,509 | B1 | 7/2004 | Griesbach et al. | |
| 6,773,898 | B1 | 8/2004 | Nyberg et al. | |
| 6,776,824 | B2 | 8/2004 | Wen | |
| 6,852,771 | B2 | 2/2005 | Balch et al. | |
| 6,927,058 | B1 | 8/2005 | Dupont | |
| 7,045,343 | B2 | 5/2006 | Witcher et al. | |
| 2001/0006818 | A1 | 7/2001 | Amhof et al. | |
| 2002/0051733 | A1 | 5/2002 | Antonoplos et al. | |
| 2002/0151084 | A1 | 10/2002 | Lippold | |
| 2003/0012688 | A1 | 1/2003 | Kippenhan, Jr. | |
| 2003/0138345 | A1 | 7/2003 | Schwabe | |
| 2003/0138347 | A1 | 7/2003 | Lin | |
| 2003/0141477 | A1 | 7/2003 | Miller | |
| 2003/0143112 | A1 | 7/2003 | Suslick et al. | |
| 2003/0190253 | A1 | 10/2003 | Kohler et al. | |
| 2003/0208165 | A1 | 11/2003 | Christensen et al. | |
| 2003/0211618 | A1 | 11/2003 | Patel | |
| 2003/0231990 | A1 | 12/2003 | Faries, Jr. et al. | |
| 2004/0001783 | A1 | 1/2004 | Bowen | |
| 2004/0052679 | A1 | 3/2004 | Root et al. | |
| 2004/0241862 | A1 | 12/2004 | Puntambekar | |
| 2004/0258562 | A1 | 12/2004 | Mills et al. | |
| 2004/0265170 | A1 | 12/2004 | Read | |
| 2005/0058821 | A1 | 3/2005 | Smith et al. | |
| 2005/0118056 | A1 | 6/2005 | Swanson et al. | |
| 2005/0130253 | A1 | 6/2005 | Lye et al. | |
| 2005/0136102 | A1 * | 6/2005 | Hoffman et al. | 424/449 |
| 2005/0163654 | A1 | 7/2005 | Stecklein et al. | |
| 2005/0169796 | A1 | 8/2005 | Krakers et al. | |
| 2005/0274055 | A1 | 12/2005 | Cook et al. | |
| 2006/0054526 | A1 | 3/2006 | Dean et al. | |
| 2006/0062687 | A1 | 3/2006 | Morales | |
| 2006/0104856 | A1 | 5/2006 | Farrell et al. | |
| 2006/0114754 | A1 | 6/2006 | MacDonald et al. | |
| 2006/0134613 | A1 | 6/2006 | Martin et al. | |
| 2006/0134728 | A1 * | 6/2006 | MacDonald et al. | 435/34 |
| 2006/0165754 | A1 | 7/2006 | Ranade | |
| 2006/0246564 | A1 * | 11/2006 | Parent et al. | B01D 53/84 435/181 |
| 2007/0048503 | A1 | 3/2007 | MacDonald et al. | |
| 2007/0282181 | A1 | 12/2007 | Findlay et al. | |
| 2007/0293818 | A1 * | 12/2007 | Stout et al. | 604/93.01 |
| 2009/0024096 | A1 * | 1/2009 | Hai | A61L 27/28 604/265 |

FOREIGN PATENT DOCUMENTS

| | | | |
|---|---|---|---|
| EP | 0803257 | | 10/1997 |
| EP | 0941740 | | 9/1999 |
| WO | 2005/059162 | | 6/2005 |
| WO | 2006/065349 | | 6/2006 |
| WO | 2006/018208 | | 8/2007 |
| WO | 2009014997 | A2 * | 1/2009 |
| WO | 2008/011581 | | 3/2010 |

OTHER PUBLICATIONS

Choi, Ho-Suk, Plasma-induced graft co-polymerization of acrylic acid onto the polyurethane surface, Surface and Coatings Technology, 182 (2004), pp. 55-64.*

Next Big Future, Single Molecule Manipulations (Nov. 10, 2006) pp. 1-12.*

Rosett, W.; Hodges, G.R. "Antimicrobial Activity of Heparin" J. Clin. Microbiol. 1980, 11 (1), 30-34.*

Abd El-Aal, R.M.; Younis, M. "Synthesis and antimicrobial activity of meso-substituted polymethine cyanine dyes" Bioorg. Chem. 2004, 32, 193-210.*

International Search Report for Corresponding International Application No. PCT/US2011/031770 dated Jun. 16, 2011.

Written Opinion of the International Searching Authority for Corresponding International Application No. PCT/US2011/031770 dated Jun. 16, 2011.

Singapore Search Report Appl. No. 201000406-7, date of mailing Mar. 1, 2011—8 pages.

Durr et al. (editors), "Photochromism Molecules and Systems," Studies in organic Chemistry 40, pp. 333-334.

Christian Decker, Recent Developments in Radiation Curing Chemistry, Processes in PhotoReactive Polymers, 1995, pp. 35-55, Chapman & Hall, New York, NY.

Hubert et al., "Design of a Solvatochromic Polymer-Based Fiber Optics Chemical Sensor for Polar Solvent Detection," Advanced Materials, vol. 7, No. 11, 1995, pp. 914-917.

The Effect of Annulation Upon the Solvatochromic Behaviour of Related Merocyanines, Marcos Caroli Rezende, J. Braz. Chem, Soc., vol. 8, No. 6, 631-635, 1997. pp. 631-635.

Krech et al., "Detection of volatile organic compounds in the vapor phase using solvatochromic dye-doped polymers," Analytica Chimica Acta, vol. 341, 1997, pp. 53-62.

International Preliminary Report on Patentability for International Application No. PCT/US2011/031770 dated Jul. 27, 2012.

Second Written Opinion of the International Preliminary Examining Authority in International Application No. PCT/US2011/021770 dated May 16, 2012.

Krishna, "Excited-State Kinetics of the Hydrophobic Probe Nile Red in Membranes and Micelles," The Journal of Physical Chemistry A, vol. 103, No. 19, May 13, 1999, pp. 3589-3595.

Albert, et al., "Cross-Reactive Chemical Sensor Arrays," American Chemical Society, Chemical Reviews, 2000, vol. 100, No. 7, pp. 2595-2626.

(56) References Cited

OTHER PUBLICATIONS

Dong Li et al., "Microsystems for optical gas sensing incorporating the solvatochromic dye Nile Red," Sensors and Actuators vol. B 92, 2003, pp. 73-80, www/elseviercom/locate/sensorb.
Krongauz, Vadim V. et al., Oxygen and Radical Photopolymerization in Films, Photoinitiated Polymerization, 2003, pp. 165-175, ACS Symposium Series 847, American Chemical Society, Washington D.C.
Toutchkine et al., "Solvent-Sensitive Dyes to Report Protein Conformational Changes in Living Cells," J. Am. Chem. Soc. JACS Articles, vol. 125, No. 14, 2003, pp. 4132-4145.
Suslick, "An Optoelectronic Nose: "Seeing" Smells by Means of Colorimetric Sensor Arrays," MRS Bulletin, Oct. 2004, pp. 720-725, www/mrs.org/publications/bulletin.
Menyhay, Steve Z., Infection Control and Hospital Epidemiology, Jan. 2006, vol. 27, No. 1, pp. 23-27.
Fiorilli et al., "Tethering of modified Reichardt's dye on SBA-15 Mesoporous Silica: The effect of the linker Flexibility" Langmuir, American Chemical Society, vol. 23, 2007, pp. 2261-2268.
International Search Report, PCT/US2008/070410, dated Feb. 23, 2010, 11 pgs.
Written Opinion of the International Searching Authority, PCT/US2008/070410, dated Feb. 23, 2010, 9 pgs.
Don—et al. (editors), "Photochromism Molecules and Systems," Studies in organic Chemistry 40, pp. 333-334 (2003).
Kaler et al., "Probing Structure of Blood Plasma Proteins with Solvatochromic Fluorescent Probes, Nile Red and Its Derivatives," SPIE, vol. 2980, pp. 484-489 (1997).

* cited by examiner

ANTIMICROBIAL HOUSING AND COVER FOR A MEDICAL DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

[This application] *The present application is a reissue of U.S. patent application Ser. No. 12/759,437, filed on Apr. 13, 2010, issued as U.S. Pat. No. 9,125,973, which* is a continuation-in-part of U.S. patent application Ser. No. 11/780,876, titled IMMOBILIZATION OF DYES AND ANTIMICROBIAL AGENTS ON A MEDICAL DEVICE, filed Jul. 20, 2007, and assigned to the assignee of the present application, the entire contents of *each of* which are hereby incorporated by reference and relied upon; [this application] *U.S. patent application Ser. No. 12/759,437* is also a continuation-in-part of U.S. patent application Ser. No. 11/780,917, entitled MEDICAL FLUID ACCESS DEVICE WITH ANTISEPTIC INDICATOR, also filed on Jul. 20, 2007, and assigned to the assignee of the present application, the entire contents of *each of* which are hereby incorporated by reference and relied upon.

BACKGROUND

The present disclosure relates generally to methods of immobilizing dyes and antimicrobial agents on a surface, especially a surface of a medical device. In particular, the disclosure relates to methods of treating a polymer surface for better attachment of antimicrobial agents onto the surface, and for the attachment of dyes to the surface. The dyes will change from a first color or appearance to a second color or appearance when they are swabbed with a disinfecting fluid, such as isopropyl alcohol (IPA) or a solution of water and IPA, especially a solution of 70% water/30% IPA.

Infections acquired at hospitals or other health care sites, nosocomial infections, are an undesirable source of distress to patients. The advent of ever-more resistant bacteria and bacteria that are resistant to multiplicities of drugs only exacerabates the problem and makes the eradication of these infections even more important. An example of one cause of such infections is a biofilm, an aggregate of microbes with a distinct architecture. A biofilm is similar to a small city with a great abundance of microbial cells, each only a micrometer or two in length. The microbes form towers that can be hundreds of micrometers high, with the "streets" between the towers being fluid filled channels that supply nutrients, oxygen, and other necessities to the biofilm communities.

Such biofilms can form on the surfaces of medical devices, especially implants, such as contact lenses, catheters or other access devices, pacemakers, and other surgical implants. The U.S. Centers for Disease Control (CDC) estimates that over 65% of nosocomial infections are caused by biofilms. Bacteria growing in a biofilm can be highly resistant to antibiotics, up to a thousand times more resistant than the same bacterium not growing in a biofilm. It would be desirable if the surfaces of these medical devices were resistant to biofilm formation and bacterial growth.

Polymers are used to make many of the diagnostic or therapeutic medical devices that are subject to biofilm formation. For example, connectors for kidney dialysis, such as peritoneal dialysis and hemodialysis may be made of polymers. Dialysate fluid containers, access ports, pigtail connectors, spikes, and so forth, are all made from plastics or elastomers. Therapeutic devices such as catheters, drug vial spikes, vascular access devices such as luer access devices, prosthetics, and infusion pumps, are made from polymers. Medical fluid access devices are commonly used in association with medical fluid containers and medical fluid flow systems that are connected to patients or other subjects undergoing diagnostic, therapeutic or other medical procedures. Other diagnostic devices made from polymers, or with significant polymer content meant for contact with tissues of a patient, include stethoscopes, endoscopes, bronchoscopes, and the like. It is important that these devices be sterile when they are to be used in intimate contact with a patient.

Typical of these devices is a vascular access device that allows for the introduction of medication, antibiotics, chemotherapeutic agents, or a myriad of other fluids, to a previously established IV fluid flow system. Alternatively, the access device may be used for withdrawing fluid from the subject for testing or other purposes. The presence of one or more access devices in the IV tubing sets eliminates the need for phlebotomizing the subject repeatedly and allows for immediate administration of medication or other fluids directly into the subject.

Several different types of access devices are well known in the medical field. Although varying in the details of their construction, these devices usually include an access site for introduction or withdrawal of medical fluids through the access device. For instance, such devices can include a housing that defines an access opening for the introduction or withdrawal of medical fluids through the housing, and a resilient valve member or gland that normally closes the access site. Beyond those common features, the design of access sites varies considerably. For example, the valve member may be a solid rubber or latex septum or be made of other elastomeric material that is pierceable by a needle, so that fluid can be injected into or withdrawn from the access device. Alternatively, the valve member may comprise a septum or the like with a preformed but normally closed aperture or slit that is adapted to receive a specially designed blunt cannula therethrough. Other types of access devices are designed for use with connecting apparatus employing standard male luers. Such an access device is commonly referred to as a "luer access device" or "luer-activated device," or "LAD." LADS of various forms or designs are illustrated in U.S. Pat. Nos. 6,682,509, 6,669,681, 6,039,302, 5,782,816, 5,730,418, 5,360,413, and 5,242,432, and U.S. Patent Application Publications Nos. 2003/0208165 and 2003/0141477, all of which are hereby incorporated by reference herein.

Before an access device is actually used to introduce or withdraw liquid from a container or a medical fluid flow system or other structure or system, good medical practice dictates that the access site and surrounding area be contacted, usually by wiping or swabbing, with a disinfectant or sterilizing agent such as isopropyl alcohol or the like to reduce the potential for contaminating the fluid flow path and harming the patient. It will be appreciated that a medical fluid flow system, such as an IV administration set, provides a direct avenue into a patient's vascular system. Without proper aseptic techniques by the physician, nurse or other clinician, microbes, bacteria or other pathogens found on the surface of the access device could be introduced into the IV tubing and thus into the patient when fluid is introduced into or withdrawn through the access device. Accordingly, care is required to assure that proper aseptic techniques are used by the healthcare practitioner. This warning applies to many medical devices, especially those in contact with the patient, and especially so for access devices that, like catheters or infusion pumps, access the patient's bodily orifices, especially those of the vascular system. Other devices that are subject to multiple touches include device covers and housings, and especially touch-screens, key pads, and user controls, such as switches, handles, and knobs.

As described more fully below, the methods for attaching antimicrobial agents and dyes that indicate that proper aseptic techniques have been used, are believed to represent important advances in the safe and efficient administration of health care to patients.

SUMMARY

One embodiment is a method for providing a cover or housing for a medical device. The method includes steps of providing a medical device cover or a housing made from a polymer, the polymer optionally including a porous surface. The method also includes steps of treating a surface of the cover or housing with a plurality of functional groups, attaching a linking group to the functional groups, and attaching an antimicrobial agent to the functional group or to the linking group.

Another embodiment is a method of treating a medical device. The method includes steps of treating a surface or porous surface of a polymeric cover or a polymeric housing for a medical device with a strong acid or plasma discharge to provide a plurality of functional groups on the surface. The method also includes steps of reacting the functional groups with a linking agent to form attachment sites, the linking agent selected from the group consisting of poly(N-succinimidyl acrylate) (PNSA), polyethyleneimine, polyallylimine, and polymers with an aldehyde functional group, and attaching a solvatochromic dye, an antimicrobial agent, or an alkyl-amino containing compound to the attachment sites.

Another embodiment is a polymeric cover or housing. The polymeric cover or housing includes a polymer in a form of a cover or a housing for a medical device, a plurality of attachment sites on an least an outer surface of the polymer, optionally, a plurality of functional groups attached to the attachment sites, and at least one of an antimicrobial compound and a solvatochromic dye, attached to the attachment sites or to the functional groups, wherein the outer surface is configured to reversibly change from a first appearance to a second appearance when the outer surface is swabbed with a disinfecting solution.

Another embodiment is a medical device. The medical device includes a porous polymeric surface or cover for a medical device, a plurality of attachment sites on the polymeric surface, optionally, a plurality of functional groups attached to the attachment sites, a solvatochromic dye, attached to the attachment sites or to the functional groups, wherein the porous polymeric surface is configured to reversibly change from a first appearance to a second appearance when the porous polymeric surface is swabbed with a disinfecting solution, and optionally an antimicrobial compound, attached to the attachment sites or to the functional groups, wherein the antimicrobial compound is configured to be cidal to, or to resist growth of, microorganisms on the polymeric surface.

Another embodiment is a medical device. The medical device includes a cover or housing for a medical device made from a polymer, a plurality of attachment sites on a surface of the cover or housing, optionally, a plurality of functional groups attached to the attachment sites, a solvatochromic dye, attached to the attachment sites or to the functional groups, wherein the surface is configured to reversibly change from a first appearance to a second appearance when the porous polymeric surface is swabbed with a disinfecting solution, and an amino-alkyl containing compound selected from the group consisting of peptides, proteins, Factor VIII or other anti-clotting Factor, polysaccharides, polymyxins, hyaluronic acid, heparin, condroitin sulfate, chitosan, and derivatives of each of these, to the attachment sites.

Additional features and advantages are described herein, and will be apparent from, the following Detailed Description and the figures.

DETAILED DESCRIPTION

Figure 1:
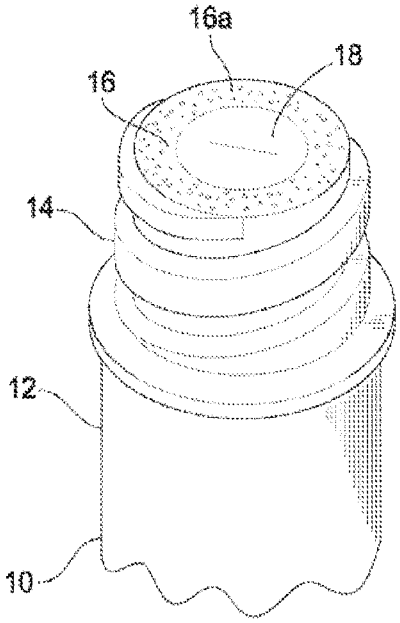
FIG. 1 is a perspective view of a medical device.

Immobilization of Dyes and Antimicrobial Agents on Polymer Surfaces

This section describes the experimental work that was done to prepare polymeric surfaces for direct attachment of dye molecules and antimicrobial agents. The substances used to prepare the surfaces function by reacting the surfaces and adding functional groups that will covalently bind the dye to the surface. Examples of dyes include Reichardt's dye and solvatochromic dyes. A solvatochromic dye changes color to alert a medical professional that the surface, such as an infusion pump housing or cover, has been swabbed and is momentarily clean. This technique is also effective in binding antimicrobial agents to the surface. Examples include chlorhexidine compounds and derivatives, such as chlorhexidine gluconate, and other antimicrobial agents bearing aminoalkyl groups. Examples also include chloroxyphenol, triclosan, triclocarban, and their derivatives, and quaternary ammonium compounds. Many other antimicrobial or oligodynamic substances may also be attached. These compounds are cidal to, or at least to inhibit the growth of harmful bacteria or other microorganisms on the surfaces to which they are applied, which is beneficial to the patient.

Materials known to have properties of resistance to such microorganisms are described and disclosed in U.S. Pat. No. 4,847,088, U.S. Pat. No. 6,663,877, and U.S. Pat. No. 6,776,824, all of which are hereby incorporated by reference in their entirety as though they were copied directly into this patent. For instance, quaternary ammonium compounds (frequently with organic or silicate side chains) are well-known for such properties, as are boric acid and many carboxylic acids, such as citric acid, benzoic acid, and maleic acid. Pyridinium and phosphonium salts may also be used. Besides organic compounds, certain non-organic materials and compounds are also known for their resistance to germs and organisms. Antimicrobial compounds are used in low concentrations, typically about from about 0.1% to 1% when incorporated into the material itself, e.g., a housing of a luer access device or other vascular access device. Antimicrobial compounds may also be used on many other medical devices, such as catheters, dialysis connects, such as those used in peritoneal dialysis, hemodialysis, or other types of dialysis treatment. They may also be applied to drug vial spikes, prosthetic devices, stethoscopes, endoscopes and similar diagnostic and therapeutic devices, and to infusion pumps and associated hardware and tubing. The use of antimicrobial compounds on these devices, among others, can help to prevent infection and to lessen the effect of infection.

Metals, especially heavy metals, and ionic compounds and salts of these metals, are known to be useful as antimicrobials even in very low concentrations or amounts. These substances are said to have an oligodynamic effect and are considered oligodynamic. The metals include silver, gold, zinc, copper, cerium, gallium, platinum, palladium, rhodium, iridium, ruthenium, osmium, bismuth, and others. Other metals with lower atomic weights also have an inhibiting or cidal effect on microorganisms in very low concentrations. These metals include aluminum, calcium, sodium, lithium, magnesium, potassium, and manganese, among others. For present purposes, all these metals are considered oligodynamic metals, and their compounds and ionic substances are oligodynamic substances. The metals and their compounds and ions, e.g., zinc oxide, silver acetate, silver nitrate, silver chloride, silver iodide, and many others, may inhibit the growth of microorganisms, such as bacteria, viruses, or fungi, or they may have cidal effects on microorganisms, such as bacteria, viruses, or fungi, in higher concentrations, such as biofilms. Because many of these compounds and salts are soluble, they may easily be placed into a solution or a coating, which may then be used to coat a medical device housing or cover, such as for a luer access device or an infusion pump. Silver has long been known to be an effective antimicrobial metal, and is now available in nanoparticle sizes, from companies such as Northern Nanotechnologies, Toronto, Ontario, Canada, and Purest Collids, Inc., Westampton, N.J., U.S.A. Other oligodynamic metals and compounds are also available from these companies.

Other materials, such as sulfanilamide and cephalosporins, are well-known for their resistance properties, including chlorhexidine and its derivatives, ethanol, benzyl alcohol, lysostaphin, benzoic acid analogs, lysine enzyme and metal salt, bacitracin, methicillin, cephalosporin, polymyxin, cefachlor, Cefadroxil, cefamandole nafate, cefazolin, cefime, cefinetazole, cefonioid, cefoperazone, ceforanide, cefotanme, cefotaxime, cefotetan, cefoxitin, cefpodoxime proxetil, cefiaxidime, ceftizomxime, cefirixzone, cefriaxone moxolactam, cefuroxime, cephalexin, cephalosporin C, cephalosporin C sodium salt, cephalothin, cephalothin sodium salt, cephapirin, cephradine, cefuroximeaxetil, dihvdracephaloghin, moxalactam, or loracarbef mafate. Microban, "Additive B," 5-chloro-2-(2,4 dichloro-phenoxy) phenol is another such material.

Functional Groups

The following portion discusses a number of processes found to be effective in providing functional groups for the attachment of the above-mentioned solvatochromic dyes and antimicrobial agents. Functional groups may include an activated carboxyl group, an activated amine group, an aldehyde group, epoxy group or alkyl halide group. The desired dye or agent may then be directly attached, or an intermediate group may be used attach the desired substance. Certain polymers, such as nylon, polycarbonate, and polyester, e.g., polyethylene terephthalate (PET), are adaptable for attachment of such agents. These structural materials, among others, are useful in making housings or containers for medical instruments, such as infusion pump housings, dialysis cassettes, housings for viewing screens or monitors, printer bodies, keyboards, keypads, and the like. These structures are desirably not hospitable environments for microbes, biofilms, or any other pathogens. Antimicrobial treatments may more easily adhere to these surfaces when treated as discussed below.

Nylon Surfaces

In one example, a Whatman nylon-6,6 membrane, pore size 0.2 μm, 47 mm, Whatman Cat. No. 7402-004, was obtained from Whatman Inc., Florham Park, N.J., USA. Other membranes are also available from Whatman, including other nylons or polyamides, polytetrafluoroethylene (PTFE or Teflon®), polyester, polycarbonate, cellulose and polypropylene. The membranes were first washed thoroughly, successively with dichloromethane, acetone, methanol and water. The membranes were then washed several times with water to achieve a neutral pH. They were finally washed in methanol and dried under high vacuum. The membranes were then treated with 3M HCl at 45° C. for four hours to yield specimen NM-1. Without being bound by any particular theory, it is believed that this resulted in the creation of a number of amino groups on the membrane surface. The free amine concentration of the untreated nylon was calculated as $6.37\times10^{-7}$ moles/cm$^2$, while the free amine concentration after acid treatment was calculated as $13.28\times10^{-7}$ moles/cm$^2$. The concentration was calculated using the method of Lin et al., described in Biotech Bioeng., vol. 83 (2), 168-173 (2003). Thus, the treatment appeared to double the concentration of free amine on the surface and available for binding.

The NM-1 membrane was then contacted with poly(N-succinimidyl acrylate) (PNSA) dissolved in dimethylformamide (DMF) by placing the membrane in a flask with the dissolved PNSA. It is expected that treatments with other polymers containing aldehyde groups, such as polyacrylaldehyde or polyacrolein, would also be effective. Triethylamine was then added to the flask, which was rotary shaken while under a continuous argon purge for about 6 hours. The treated nylon membrane was then thoroughly washed with DMF to produce N-succinimidyl carboxylate groups on the surface of the nylon, forming NM-2. The di(trifluoroacetate) salt of 4,6-dichloro-2-[2-(6-amino-hexyl-4-pyridinio)-vinyl] phenolate was dissolved in DMF and was converted by neutralization of the trifluoroacetate counter ions with triethylamine. The previously-treated membrane was added to the reaction flask and was rotary-shaken overnight. The resulting membrane, NM-3, with the salt of 4,6-dichloro-2-[2-(6-amino-hexyl-4-pyridinio)-vinyl]phenolate on its surface, was then thoroughly washed with DMF. The surface of the membrane was a light purple when dry. The same surface turned dark purple when swabbed with isopropyl alcohol, and turned a salmon color when swabbed with a mixture of isopropyl alcohol containing about 30% water.

It is believed that the NM-3 membrane had excess N-succinimidyl carboxylate on its surface. It is also believed that this excess would hydrolyze and protonate the dye at the phenolate position, rendering the dye colorless. A number of NM-3 membranes were treated with different amines to stabilize the carboxyl groups and also to discover what colors or other properties would result from the use of different amines. A series of membranes. NM-4 to NM-9 were treated with different amines, resulting in membranes with more stable surfaces but with only slightly different colors. The particular amine was dissolved in methanol, the membrane was added to the reaction flask, and the flask was rotary shaken overnight. The resulting membrane was then washed with acetone and dried under vacuum. Table 1 below summarizes the different used amines and the resulting properties. These results suggest that a number of amino and ammonium compounds may be used to provide attachment sites, including primary amines, ammonium hydroxide, amine ($NH_2$)— terminated compounds and polymers, morpholine, and an aromatic primary amine.

The membranes had pores on the order of 0.2 μm, resulted in rapid color changes when swabbed, and returned to the dry color within a minute or two. As noted, it is believed that the NM-3 membrane had an excess of N-succinimidyl carboxylate groups on its surface. Therefore, an antimicrobial agent, chlorhexidine, was applied. Chlorhexidine was dissolved in methanol, the membrane was added to the reaction flask, and the flask was rotary shaken overnight. The membrane was thoroughly washed with acetone and dried under vacuum. It is believed that this membrane, NM-10, now contained both antimicrobial agent and dye. The membrane was tested. Its dry color was a moderate purple, turning to a dark purple in isopropyl alcohol (IPA) and to a moderate orange/red in 70% IPA.

TABLE 1

Amine Treatment of Nylon Membranes

| Nylon Membrane-Number | Amine used | Amine dose, mmol. | reagent soln, ml | Soln pH | Color, dry | Color, IPA | Color, IPA + 30% water |
|---|---|---|---|---|---|---|---|
| NM-4 | 2-methoxyethylamine | 15 | 7.50 ml DMF | 11.5 | Very, wry light pink | Light brown/pink | Light brown/pink |
| NM-5 | Hexylamine | 15 | 7.50 ml DMF | 12 | Very, very light brown/pink | Light brown/pink | Light brown/pink |
| NM-6 | Benzylamine | 15 | 7.50 ml DMF | 11.5 | Very light pink | Light brown/pink | Light brown/pink |
| NM-7 | Morpholine* | 15 | 7.50 ml DMF | 10 | Moderate purple | Dark purple | Salmon |
| NM-8 | Ammonium hyroxide | excess | 20 ml $NH_4OH$ | ND** | Moderate purple | Dark purple | Salmon |
| NM-9 | 3-aminopropyl-terminated poly-dimethylsiloxane | 3.51 | 10 ml toluene | 10 | Light purple | Moderate purple | Moderate salmon |

*NM-7 had an additional 0.1 ml triethylamine added, with a final pH of 11- to 11.5.
**The pH of the NM-8 solution was not determined.

Polycarbonate Surfaces

A second series of plastic surfaces was also tested. DE1-1D Makrofol® polycarbonate films, 0.005 inch thick, clear-gloss/gloss, were obtained from Bayer Polymers Division, Bayer Films Americas, Berlin, Conn., USA. The films were cut into 1 cm squares and were treated with 4 ml of a solution of 0.25 M chlorosulfonic acid in ethyl ether. The square and the solution were placed in a screw-cap vial and cooled to about 5° C. and rotary shaken for 1 hour. The resulting chlorosulfonated film was thoroughly washed with ethyl ether to yield membrane PC-1. It is believed that the amino end groups on the 4,6-dichloro-2-[2-(6-amino-hexyl-4-pyridinio)-vinyl] phenolate dye would react with the chlorosulfonyl groups which had been attached to the polycarbonate surface. A solution of the dye was prepared by dissolving 10 mmol in ethanol and treating with 0.22 mmol triethylamine. The resulting dye solution had a pH of 9.7. The PC-1 film was then added to a rotary flask containing the dye and was rotary shaken overnight and then washed thoroughly with methanol to yield film PC-2. The dry film had a moderately pinkish/purple color. When wetted with 70% IPA, it turned to a peach color.

Other films treated in the same manner, but with a four-hour chlorosulfonic acid treatment, had no color change activity. It is believed that the chlorosulfonyl moiety is a temporary transition product that converts to a more stable entity over time, and thus is not available for attachment of the dye. Other experiments included varying the time for dye attachment from 1 day to 5 days. The films treated for longer periods of time also had more intensely-colored surfaces. Due to the solubility of PC in other solvent, only ethyl ether was used for this experiment. The color change in the polycarbonate film, with very low porosity, was much slower than the color change in membranes, which have a high and regulated porosity. Treatment of polycarbonate surfaces with methacrylic acid or acrylic acid is expected to add carboxyl functional groups to the surface.

Polyester Surfaces

Polyester surfaces were also obtained and tested, e.g., Millipore polyethylene-terephthalate (PET) membranes were obtained, Cat. No. T6PN1426, from Millipore Corp., Billerica, Mass., USA. These membranes were 47 mm in diameter, 0.013 mm thick, with pores having a nominal diameter of 1.0 μm. The membranes were cut into 3 cm×3 cm squares and added to a solution of water and acetone in a screw-cap bottle. 7.5 mmol of methacrylic acid, followed by 0.090 mmol of benzoyl peroxide in 2 ml acetone, were added to the solution. The bottle was rotary shaken at 85 C for 4 hours. The resulting membrane was thoroughly washed several times with hot water, followed by acetone, and then dried under vacuum to yield membrane PET-1. Without being bound to any particular theory, it is believed that this treatment results in the grafting of poly(methacrylic acid) to benzene ring of PET. The membranes were tested, and treatment by methacrylic acid resulted in weight gains of 50-53 percent. It is also believed that the subsequent treatment with benzoyl peroxide results in attachment of poly (methacrylic acid) to the polyester or PET surface. At least some of the attachments may be of a polymeric rather than monomeric nature, i.e., the attachments may be at least short chains with multiple carboxyl terminations. The terminal amine groups of a solvato-chromic dye, 4,6-dichloro-2-[2-(6-amino-hexyl-4-pyridinio)vinyl]-phenolate dye, or of an antimicrobial agent, can then attach to the carboxyl groups, as amide linkages.

A solution of the was prepared as follows for the PET membranes. 0.25 mmol of the di(trifluoroacetate) salt was dissolved in 10 ml of DMF, to which was added 0.51 mmol of triethylamine. 0.30 mmol of EEDQ (2-ethoxy-1-ethoxy-carbonyl-1,2 dihydroquinoline) coupling agent was added. The PET-1 membrane was added to this reaction solution and was rotary shaken overnight. The resulting membrane was thoroughly washed with methanol. This membrane had a light orange/red color. It is believed that the residual carboxyl groups may protonate the phenolate moiety of the dye, rendering it colorless. Therefore, the membrane was surface-treated with a 5% sodium bicarbonate solution to convert any remaining carboxyl groups to the sodium salt. The membrane was then washed with water, followed by methanol, and dried under vacuum to yield the PET-2 membrane. The dry film was orange/red. When wetted with 70% IPA, the membrane became a light salmon color, and changed to a salmon color when tested with IPA alone. In further experiments, it was found that increasing the treatment time of the membrane by the dye solution caused a more intense coloration of the membrane.

In addition to the treatments discussed above for specific structural plastics, other treatments may be used. For example, polycarbonate materials may be cleaned on their surface and then treated with polyethyleneimine or polyallylimine to prepare the surface by forming what is believed to be a polycarbonate/polyethyleneimine conjugate or linking group or a polycarbonate/polyallylimine conjugate or linking group. The material is then treated with an appropriate antimicrobial compound, a solvatochromic dye, or both.

The results of these tests demonstrate that several substrates are suitable for the attachment of solvatochromic dyes or antimicrobial agents or compounds, or may be treated so that the dyes or antimicrobials easily attach. In addition to the particular materials tested, urethane membranes and foams may be used, perhaps without any treatment because of the —NHCOO— functional groups inherent in urethanes. These results demonstrate that discrete, small rings or membranes, such as those cut from a sheet, may be used. Other polymeric surfaces useful in embodiments include thin films, cast films, molded or shaped parts, or even thin coatings intended for placement on another object, for example, a medical device housing or cover, such as a luer access device, an infusion pump, or a catheter.

Acrylic membranes or coatings may be used, at least for Reichardt's dye, without treatment. The presence of polyester-like RCOO— groups in acrylic polymers renders them suitable from the start for attachment of amine-containing dyes or antimicrobials, as well as other dyes. Urethane membranes or foams may be used as is, or they may be treated to make them even more suitable for dye or antimicrobial attachment. Polyimides may suitable if they are flame- or plasma treated, or if foamed polyimides are used. Melamines, maleic anhydride derivatives, blends and co-polymers may also be useful, as may blends, co-polymers and composites of any of these materials. Silicones are less amenable to treatment, however, foamed silicones may be used. For example, treating silicone with 5-10 M NaOH for several hours forms Si—OH (silanol) groups, which can then be used to form carboxyl or other functional group attachment sites.

Solvatochromic Dyes Useful as Antiseptic Indicators

The synthesis of a solvatochromic dye that has been found useful as an antiseptic indicator was previously disclosed in U.S. patent application Ser. No. 11/780,876, to which this patent claims priority and which is incorporated by reference in its entirety. The synthesis was carried out in a number of steps, resulting in compound 1 below:

Compound 1

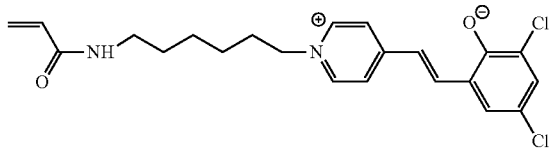

Without being bound to any particular theory, the solvatochromic activity is believed to be due at least in part, to the portion of the molecule between the phenolate ring and the pyridine ring. Accordingly, it has been found that substitution of a hydrogen atom for the acrylamido group does not adversely affect the solvatochromic activity of the dye. The structure of the this molecule, 4,6-dichloro-2-[2-(6-aminohexyl-4-pyridinio)vinyl]phenolate compound 2, is shown below, after neutralization and removal of the trifluoroacetate counterions. In one sense, compound 2 below is compound 1 with a hydrogen substituting for the acryl group.

Compound 2

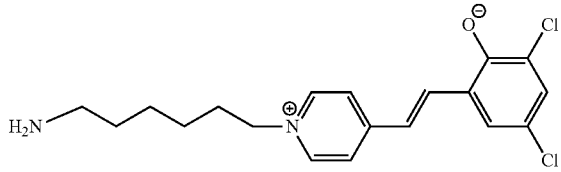

Compound 2 is more easily handled as a salt, which may be the HCl, HBr, HF, phosphate, sulfate, or other salt, so long as the species is not carboxylated, as described in the referenced document.

Other substitutes as shown below on compound 3, R1, on the amine group nitrogen atom include at least the halogens, chloride, bromide, fluoride, iodide, and alkyl mercapto. Alkyl mercapto groups, such as ethyl mercapto, and non-bending aromatic bridge groups, such as aromatic mercaptan, are also suitable. It is also possible that at least short chain alkoxy derivatives, such as C3 through C6, especially C3 and C6, are suitable. A hexyl group between the amine group and the pyridine ring worked well. Other short chain aliphatic molecules may also be used in these solvatochromic dyes, such as isohexyl, pentyl, isopentyl, butyl, isobutyl, and decyl and many others, up to $C_{20}$, i.e., $C_4$ to $C_{20}$ aliphatic.

It is also believed that aliphatic species are required. Other molecules that will perform well as a solvatochromic dye include substitution of ethene group between the pyridine ring and the benzene ring by conjugated double bonds of butadiene, —C═C—C═C— or hexatriene, —C═C—C═C—C═C—. Other embodiments may include substitutions on the benzene ring, as shown below in structure 3. Either or both of the chlorides at R4, R6, may be replaced by iodide, bromide, or fluoride. The $O^-$ group in the 7-position could instead be placed in the 5-position between the chlorides. It is possible that nitrate, —$NO_2$, alkoxy, such as methoxy, ethoxy, may also yield a solvatochromic dye. Note that a number of substations on the benzene ring are readily available. For example, several salicylaldehyde compounds with halogen atoms in the 3, 5 positions are readily available from manufactures, such as Sigma-Aldrich, St. Louis, Mo., USA. When the salicylaldehyde molecule reacts with its aldehyde functionality to the pyridine ring on structure 5, the 3, 5 positions on the salicylaldehyde molecule become the 4, 6 positions on the phenol/phenolate product formed. Of course, R1 may be amine or acrylamido, R2 is C4 to C20 aliphatic, R3 is ethene, butadiene, or hexatriene, R4 and R6 are as discussed above, and R5 may be one of hydrogen and $O^-$ and R7 may be the other of hydrogen and $O^-$.

Compound 3

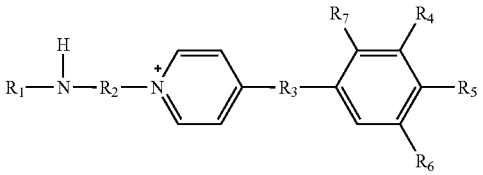

It is possible to incorporate the dye into a coating, preferably a permeable coating, which may be applied to luer access device (LAD) housings or other medical device housing or cover. LAD housings are typically made from polycarbonate (PC), but they may also be made from elastomers and other plastics, such as acrylic (e.g., PMMA), acrylonitrile butadiene styrene (ABS), methyl acrylonitrile butadiene styrene (MABS), polypropylene (PP), cyclic olefin copolymer (COC), polyurethane (PU), polyvinyl chloride (PVC), nylon, and polyester including polyethylene terephthalate) (PET). There are many coatings that will firmly adhere to the above mentioned plastics, including epoxies, polyesters, and acrylics. An example of a medical device, a vascular access device, is seen in FIG. 1. Luer access device 10 includes a housing 12, male luer connector threads 14, a rim 16, and a septum 18. Rim 16 is porous and includes a swab-access dye, shown as a dotted surface 16a. Rim 16 and rim surface 16a have been treated so that antimicrobial compounds and dyes will attach to the outer surface 16a.

Figure 2:
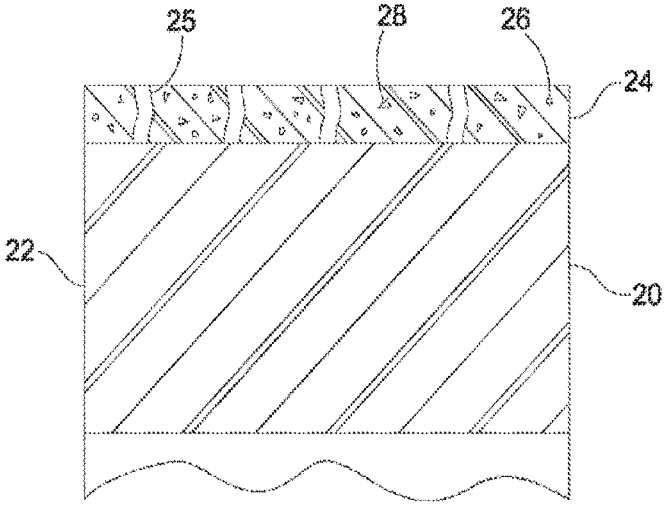
FIG. 2 is a cross-sectional view of a medical device.

FIG. 2 depicts a medical device 20 with housing 22 and a porous surface layer 24. The pores are shown as narrow channels 25 in the surface layer 24. The porous surface layer may include effective amounts of the dye 26, about 0.1 to about 1.0% by weight, and may also include small amounts of antimicrobial or oligodynamic compounds 28. There are many ways to make compounds porous, e.g., by purchasing membranes with known pore size and density, by applying solvents in the well-known TIPS (thermal inversion phase separation) process, or by inducing surface crazing or cracking into the surface. Polycarbonate membranes with tailored pore sizes may be purchased from Osmonics Corp., Minnetonka, Minn., U.S.A., and polyethylene membranes may be purchased from DSM Solutech, Eindhoven, the Netherlands. Pore sizes may vary from 1 μm down, preferably 0.2 μm down. This small pore size, and smaller, is sufficient to allow permeability to antimicrobial swabbing solutions, but large enough to prevent access by many microorganisms, which tend to be larger than 0.2 μm diameter. Many of these techniques are described in the above-mentioned related patent applications, all of which were previously incorporated by reference.

Figure 3:
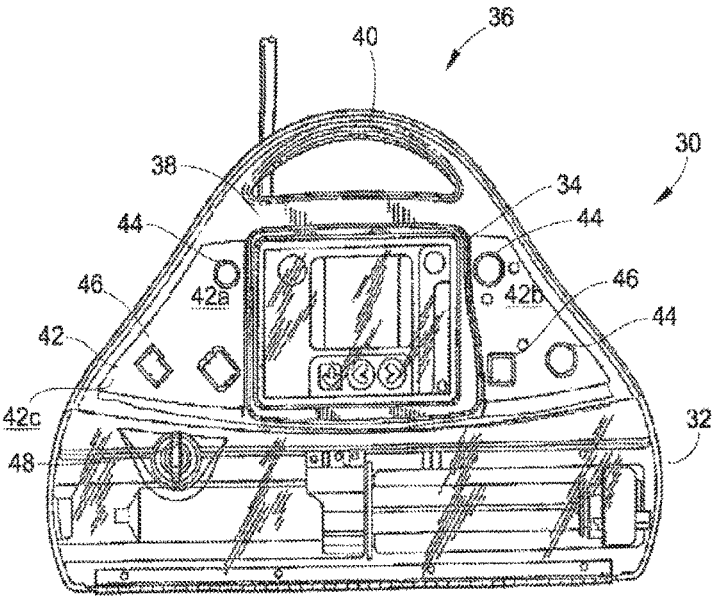
FIG. 3 is a perspective view of a medical housing and cover.

It is also possible to incorporate the dye or the antimicrobial compound into onto a cover or housing for the device. For example, FIG. 3 depicts an infusion pump 30, as described in U.S. Pat. No. 7,018,361, which is assigned to the assignee of the present patent, and which is hereby incorporated by reference in its entirety. Infusion pump 30 includes a housing 32, a control panel 34 with a small keypad (note arrows), an output screen 36 and a handle 40. Depicted in FIG. 3 is a thin, transparent outer cover 38 over substantially the control panel 34 and screen 36. Also depicted is a second transparent cover 42 which covers a broader area of the surface of infusion pump 30. Cover 42 also covers control input knobs 44 and switches 46. Cover 42 covers the left and right sides 42a, 42b, of the pump top surface and a narrow connecting portion 42c. A separate film or cover may be used for rotary switch 48.

Note that in this application, one or more users will naturally tend to touch, and possibly contaminate the outer features or surfaces with which they will be in contact, such as the handle 40, control panel 34, knobs 44, switches 46, and rotary switch 48, as well as the housing 32 itself, for example, when moving or positioning the infusion pump. These features are the ones which should thus be covered with an antimicrobial plastic or elastomeric film. Alternatively, these features themselves should be made from a polymer material with an antimicrobial treatment or coating.

Since the infusion pump may have more than one operator, nurse, or patient in contact with housing 30, control panel/keypad 34, or screen 36, cover 38 is thin and is easily removed and replaced. Cover 42 is also thin and easily replaced. A removable, antimicrobial cover will remove one cause of infection among patients, or at least one cause of transfer of germs or other microbes. As described below, the polymeric housing, its surface, or the removable cover may be made from a plastic or an elastomeric material. The housing, its surface or the cover may incorporate a surface coating of the antimicrobial compound, as described below. The device may be prepared, as also described below, to immobilize an antimicrobial agent on the surface. This keeps the antimicrobial compounds on the surface where they are most likely to encounter microbes, rather than within the body of the polymer.

The cover 42 is made from an inexpensive, transparent polymer that naturally clings to the surface of the pump. Such polymers include thin films of polyethylene, polypropylene, and PVC. Also useful in such applications, but opaque, are elastomers, such as silicone, polyurethane, and nitrile. The polymers need not be sterilizable because they are disposed after a set period of time, such as after a shift at a hospital or other care center. Alternatively, they may also be changed after an interval, such as after every user. As discussed above, the housing 32 is made from a structural and medically acceptable plastic that is suitable for the application. These structural materials include nylon, polycarbonate, PET, and many other materials that can accept an anti-microbial treatment or coating.

Other embodiments are described in related application, MEDICAL FLUID ACCESS DEVICE WITH ANTISEPTIC INDICATOR, U.S. patent application Ser. No. 11/780,917, which is assigned to the assignee of the present patent, the entire contents of which are hereby incorporated by reference. Surface 16a is porous or permeable and the polymer from which the surface is made preferably has an index of refraction from about 1.25 to about 1.6. The permeable surface is typically opaque and may incorporate a small amount of dye. The amount of the dye, such as from about 0.1% to about 1%, is effective in adding a color to the surface, or rendering the surface a translucent with a tint or hint of color.

The surface is porous, so that a disinfecting or antiseptic swabbing solution, such as IPA or a 70% IPA/30% water solution, will permeate the surface. The disinfecting solution may also contain an antimicrobial compound, such as chlorhexidine. If the index of refraction of the swabbing solution, about 1.34, matches or is close to the index of refraction of the polymer from which the porous surface is made, the surface will become transparent, if there is no dye. If a dye is present, the surface will change color as the dye changes state from a first pH to a second, different pH, the pH of the swabbing solution. Solutions or swabbing compounds other than IPA and water may be used, although theses are the most common. For example, ethanol has a refractive index of 1.36. Additions to the swabbing solution, such as chlorhexidine, will also vary the refractive index, thus allowing users to tailor the swabbing solution to insure a visually distinct appearance change, whether from opaque to transparent or from one color to another.

Tetrazolium Salts

In addition to these antimicrobial compounds, tetrazolium compounds and their derivatives, such as their salts, may be used, especially on the surfaces of medical devices, and on their housings and covers. These compounds are initially colorless, but in contact with viable bacteria they enter into the bacteria and are converted by an enzyme (Dehydrogenase) to colored Formazan. The color change is used for microbial detection. Depending on the structure of the substituent on tetrazolium ring, Formazan can be red, blue, purple, brown or fluorescent. These compounds often have, or can be modified to include, a functional group suitable for binding to a polymeric surface, such as a carboxyl group, —COOH, or an amino group, —$NH_2$. In one embodiment, tetrazolium salts have the general structure shown below, compound 4, wherein $R_2$, $R_3$ and $R_5$ independently represent substituted phenyl group, 4,5-dimethylthiazolyl group or cyano group.

Compound 4

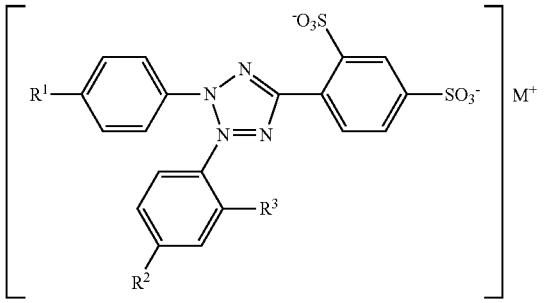

The tetrazolium salt can be modified to bear a long chain or tether terminated with an active function group, such as the above-mentioned amino or carboxyl group, so that the structure is used to immobilize the compound to a medical device surface as described above for nylon, polycarbonate, or polyester (PET) surfaces. For example, a tetrazolium salt can be reacted to form TTC, MTT, or CTC derivates. TTC is 2,3,5-triphenyl-tetrazoliumchloride. MTT is 3-(4,5-dimethylthiazol-2-yl)-2,5-diphenyl-tetrazolium bromide. CTC is 5-cyano-2,3-ditolyl tetrazoloium. Examples of these structures are depicted below as, respectively, Structures 5, 6, and 7, where n≥0 and X═Cl—, Br—, I—. As will be readily apparent to those with skill in the art, structure 5 and its derivatives are commonly known as the dye red Formazan. Structure 6 and its derivatives are known as deep blue Formazan, and structure 7 and its derivative as red fluorescent Formazan. The Formazans are inherently antimicrobial, at least when water-insoluble Formazans crystallize and accumulate inside bacteria or in a biomass such as a biofilm. It is believed that Formazans are cidal to microorganisms because they induce cellular-organelle crystallization-induced death (COCID).

Compound 5 and derivatives:

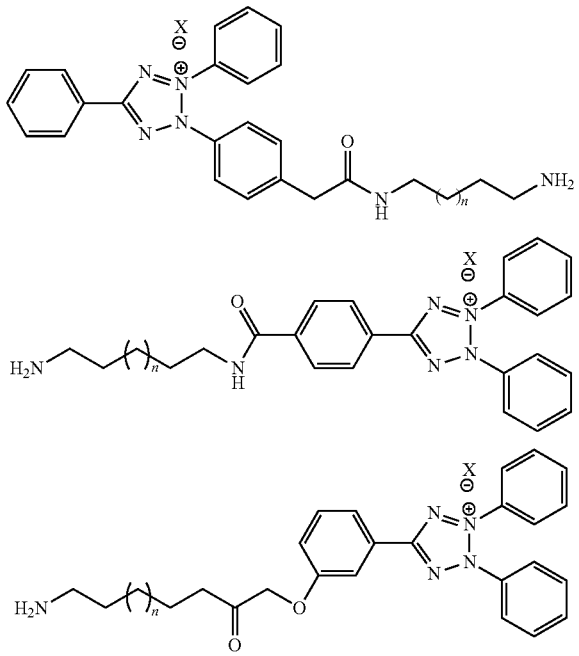

Compound 6 and derivatives

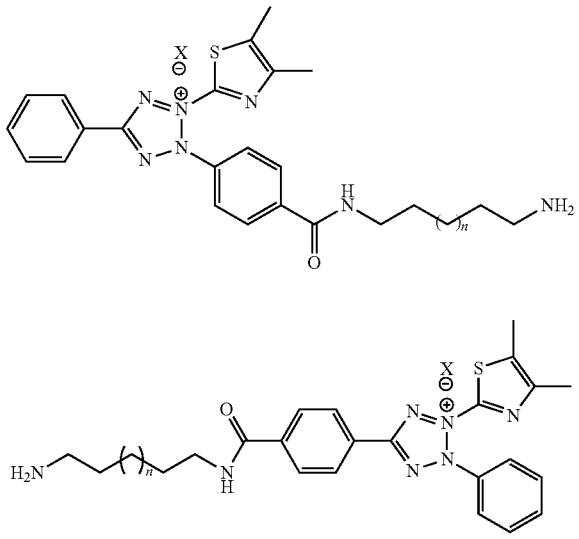

-continued

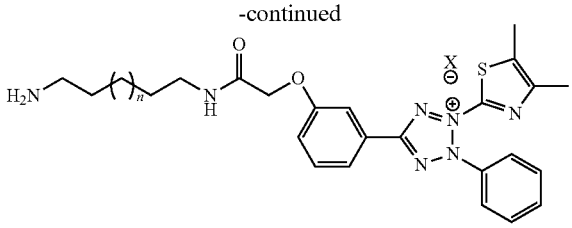

Compound 7 and derivative

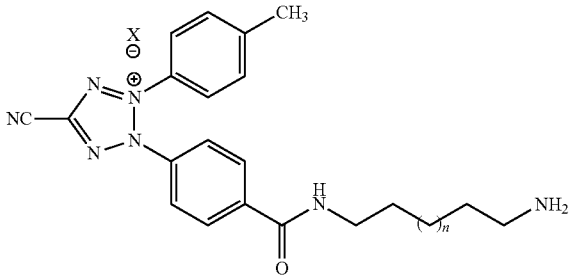

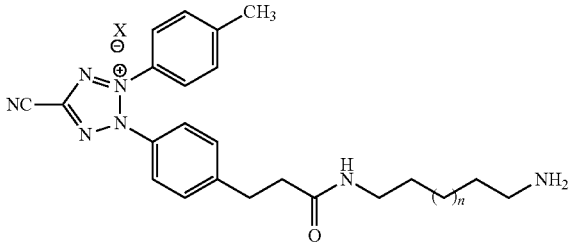

These structures are achieved according to the synthetic scheme below.

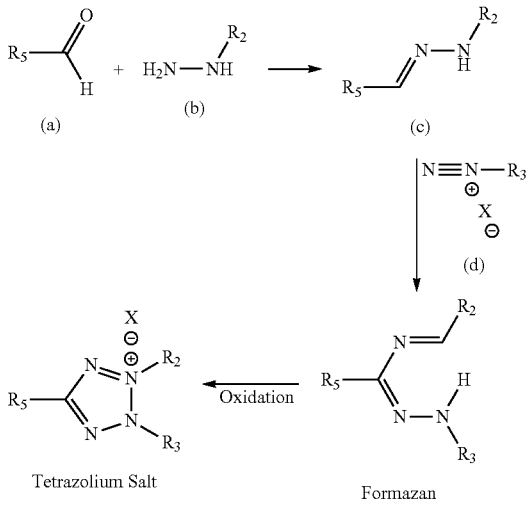

The Formazan are prepared by the condensation of appropriate diazolium chloride (d) with phenylhydrazone (c) which is obtained by condensation of aldehyde (a) and hydrazine (b). Oxidation of Formazan produces tetrazolium salt. Aryl aldehyde (a), arylhydrazine (b) and diazolium salt (d) are commercially available. The X (chloride, bromide or iodide) salt of tetrazolium salt is water soluble/solvent soluble and can be attached to the polymeric housing or cover through amide linkage using amino alkyl tether.

Solvatochromic Dyes

The dyes described above, Reichardt's dye, 4,6-dichloro-2-[2-(6-acrylamido-hexyl-4-pyridinio)vinyl]phenolate, and 4,6-dichloro-2-[2-(6-amino-hexyl-4-pyridinio)vinyl]phenolate, are only a few of many examples of useful solvatochromic dyes that may be used in these applications. There are many other solvatochromic dyes that could be used. As noted above, the principal requirements are the ability to reversibly change color when swabbed, e.g., with IPA. Without being bound to any particular theory, it is believed that the conjugation between the pyridine ring and the benzene ring, with the intermediary double bond, whether one, two, or three, that accounts for the solvatochromic activity in the new structures. Since these structural features are present in merocyanine dyes, it is believed that a number of these dyes would also be effective as indicators for swabbing, whether incorporated into a coating, as the acrylics described above, or used as part of a surface treatment. Of course, merocyanine dyes typically have a phenoxide ring, rather than a substituted benzene ring. The phenoxide ring functions as the aromatic donor and the pyridine or pyridinium ring functions as the acceptor. Of course, in the new structures, the benzene ring is the donor and the pyridine ring is the acceptor. Thus, it is believed that merocyanine dyes, compound 8 below, with conjugated pyridinium-phenoxide rings (having resonance with a pyridine-benzene structure)

Compound 8

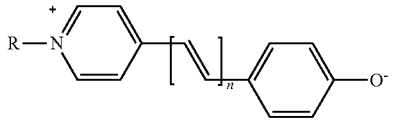

are also suitable, where n is an integer, including 0, and R is an alkyl or aryl group. Examples include 1-methyl-4-(4'-hydroxybutyl)pyridinium betaine and Brooker's merocyanine dye, 4'-hydroxy-1-methylstilbaxolium betaine.

Other solvatochromic dyes may also be used, such as an abundance of previously-known dyes, and for which the small change from their normal environment to a slightly acidic environment, such as the 6-7 pH range of IPA, will produce a color change. The table below lists a number of these dyes and their colors before and after. Note that the "before" environment of the coating or LAD housing material may be altered, such as by making it basic, by simple adjustments during the formation of the coating, the method of treating the surface, or the species used for attaching the dye. A few examples of solvatochromic dyes are presented in Table 2 below.

TABLE 2

Solvatochromic Dyes

| Dye | First state pH | Color | Second state, pH | Color |
|---|---|---|---|---|
| Bromocresal purple | 6.8 | blue | 3.2 | yellow |
| Bromothymol blue | 7.6 | blue | 6.0 | yellow |
| Phenol red | 6.8 | yellow | 8.2 | red |
| Cresol red | 7.2 | red | 8.8 | Red/purple |
| Methyl red | 4.2 | pink | 6.2 | yellow |
| Reichard's Dye | Unk | green | 6-7 | dark blue |
| Morin hydrate | 6.8 | red | 8.1 | yellow |
| Disperse orange 25 | 5.0 | yellow | 6.8 | pink |
| Nile red | Unk | Blue/purple | 6-7 | bright pink |

These and many other solvatochromic and merocyanine dyes many be used in applications according to this application. Other solvatochromic dyes include, but are not limited to, pyrene, 4-dicyanmethylene-2-methyl-6-(p-dimethyl-aminostyryl)-4H-pyran; 6-propionyl-2-(dimethyl-amino) naphthalene; 9-(diethyl-amino)-5H-benzo[a]phenoxazin-5-one; phenol blue; stilbazolium dyes; coumarin dyes; ketocyanine dyes, Reichardt's dyes; thymol blue, congo red, methyl orange, bromocresol green, methyl red, bromocresol purple, bromothymol blue, cresol red, phenolphthalein, seminaphthofluorescein (SNAFL) dyes, seminaphtharhodafluor (SNARF) dyes, 8-hydroxypyrene-1,3,6-trisulfonic acid, fluorescein and its derivatives, oregon green, and a variety of dyes mostly used as laser dyes including rhodamine dyes, styryl dyes, cyanine dyes, and a large variety of other dyes. Still other solvatochromic dyes may include indigo, 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl) julolidine (DCVJ); phenol blue; stilbazolium dyes; coumarin dyes; ketocyanine dyes; N,N-dimethyl-4-nitroaniline (NDMNA) and N-methyl-2-nitroaniline (NM2NA); Nile blue; 1-anilinonaphthalene-8-sulfonic acid (1,8-ANS), and dapoxylbutylsulfonamide (DBS) and other dapoxyl analogs. Other suitable dyes that may be used in the present disclosure include, but are not limited to, 4-[2-N-substituted-(1,4-hydropyridin-4-ylidine)ethylidene]cyclohexa-2,5-di-en-1-one, red pyrazolone dyes, azomethine dyes, indoaniline dyes, and mixtures thereof.

Other merocyanine dyes include, but are not limited to, Merocyanine dyes (e.g., mono-, di-, and tri-merocyanines) are one example of a type of solvatochromic dye that may be employed in the present disclosure. Merocyanine dyes, such as merocyanine 540, fall within the donor—simple acceptor chromogen classification of Griffiths as discussed in "Colour and Constitution of OrganiC Molecules" Academic Press, London (1976). More specifically, merocyanine dyes have a basic nucleus and acidic nucleus separated by a conjugated chain having an even number of methine carbons. Such dyes possess a carbonyl group that acts as an electron acceptor moiety. The electron acceptor is conjugated to an electron donating group, such as a hydroxyl or amino group. The merocyanine dyes may be cyclic or acyclic (e.g., vinyl-alogous amides of cyclic merocyanine dyes). For example, cyclic merocyanine dyes generally have the following structure of compound 9, in association with compound 8 above:

Compound 9

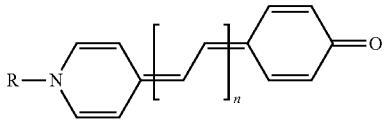

where n is an integer, including 0, and R is an alkyl or aryl group. As indicated above by the general structures of compounds 8 and 9, merocyanine dyes typically have a charge separated "zwitterionic") resonance form. Zwitterionic dyes are those that contain both positive and negative charges and are net neutral, but highly charged. Without intending to be limited by theory, it is believed that the zwitterionic form contributes significantly to the ground state of the dye. The color produced by such dyes thus depends on the molecular polarity difference between the ground and excited state of the dye. One particular example of a merocyanine dye that has a ground state more polar than the excited state is set forth above as compounds 8 and 9.

The charge-separated left hand canonical 8 is a major contributor to the ground state, whereas the right hand canonical 9 is a major contributor to the first excited state. Still other examples of suitable merocyanine dyes are set forth below in the following structures 10-20, wherein, "R" is a group, such as methyl, alkyl, aryl, phenyl, etc. See Structures 10-20 below.

Structure 10

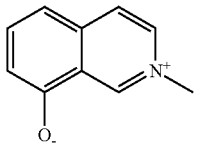

Structure 11

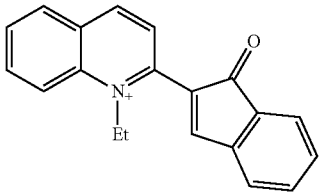

Structure 12

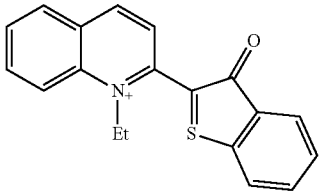

Structure 13

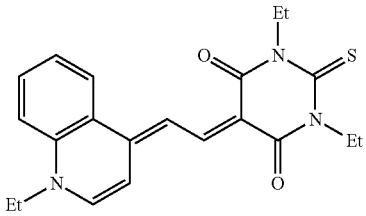

Structure 14

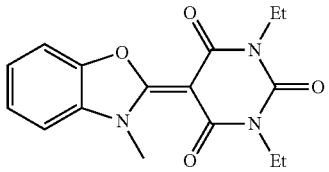

Structure 15

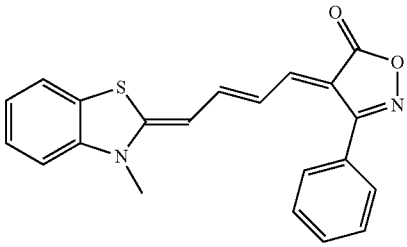

Structure 16

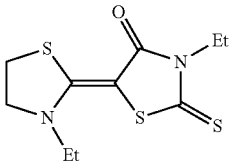

-continued

Structure 17

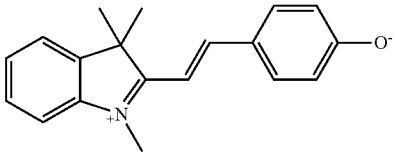

Structure 18

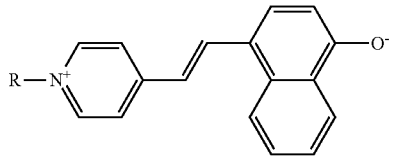

Structure 19

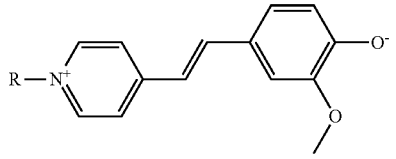

Structure 20

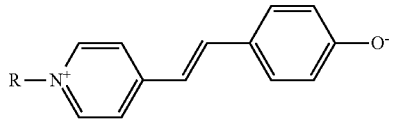

In addition to dyes and antimicrobial compounds, the preparations discussed herein may be used to attach to desired surfaces other compounds or substances containing amino alkyl groups. Examples of these types of compounds include polyethylene glycol) (PEG)-containing amino alkyl groups, peptides including antimicrobial peptides, proteins, Factor VIII, polysaccharides such as heparin, chitosan, hyaluronic acid derivatives containing amino alkyl groups, and condroitin sulfate derivates containing amino alkyl groups. One example of a protein is albumin, and an example of a peptide is polymyxin. The one thing these compounds have in common is an amino alkyl group, such as the amino alkyl group discussed above in the dye, 4,6-dichloro-2-[2-(6-aminohexyl-4-pyridinio)vinyl]phenolate.

Per the discussion above for surface preparation, the same preparation used to attach dyes and antimicrobial compounds containing alkyl amino groups will be suitable for these additional compounds. The amino alkyl groups will bind to the N-succinimidyl carboxylate groups. One technique for treating these groups is to clean the surface, followed by treatment with acid at elevated temperature, and then contacting the surface with poly(N-succinimidyl)acrylate (PNSA). It is believed that this induces carboxylate groups on the nylon surface, suitable for binding to aminoalkyl groups. Other methods are also described. For polycarbonate surfaces, treating with chlorosulfonic acid followed by washing is believed to induce chlorosulfonyl groups. These are suitable for binding by aminoalkyl groups. The treatment above of the PET surfaces is believed to result in attachment of carboxyl groups to the surface, making the also suitable for attachment of aminoalkyl groups.

Thus, polymeric surfaces as described above may also be used for attachment of peptides, proteins, Factor VIII or other anti-clotting Factors, polysaccharides, polymyxins, hyaluronic acid, heparin, chitosan, condroitin sulfate, and derivatives of each of these.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of treating a medical device, the method comprising:

providing a plurality of functional groups on a surface or porous surface of a polymeric cover or a polymeric housing for a medical device;

reacting the functional groups with a linking agent to form attachment sites, the linking agent comprising polymers with an aldehyde functional group; and attaching a solvatochromic dye to the aldehyde functional groups.

2. The method of claim 1, wherein the polymeric cover or housing has an index of refraction from about 1.25 to about 1.6.

3. The method of claim 1, further comprising treating the surface or porous surface to induce amine functional groups.

4. The method of claim 1, wherein the solvatochromatic dye is selected from the group consisting of 4,6-dichloro-2-[2-(6-aminohexyl-4-pyridinio)-vinyl]phenolate and derivatives, Reichardt's dye, its salts and derivatives, merocyanine dyes and their derivatives, and tetrazolium compounds and their derivatives.

5. The method of claim 1, further comprising stabilizing the surface or porous surface by converting unreacted carboxyl attachment sites to a salt.

6. The method of claim 1, wherein the surface or porous surface comprises a membrane or a coating for attachment to the medical device.

7. The method of claim 1, wherein the surface or porous surface is selected from the group consisting of nylon, polycarbonate, and polyester and wherein treating the nylon surface with a strong acid results in amino functional groups, treating the polycarbonate surface with chlorosulfonic acid results in sulfonyl chloride functional groups, and treating the polyester surface or polycarbonate surface with an acrylic or methacrylic acid results in carboxyl functional groups.

8. The method of claim 1, wherein the surface or porous surface is treated with a strong acid to provide the plurality of functional groups.

* * * * *